Figure 1:
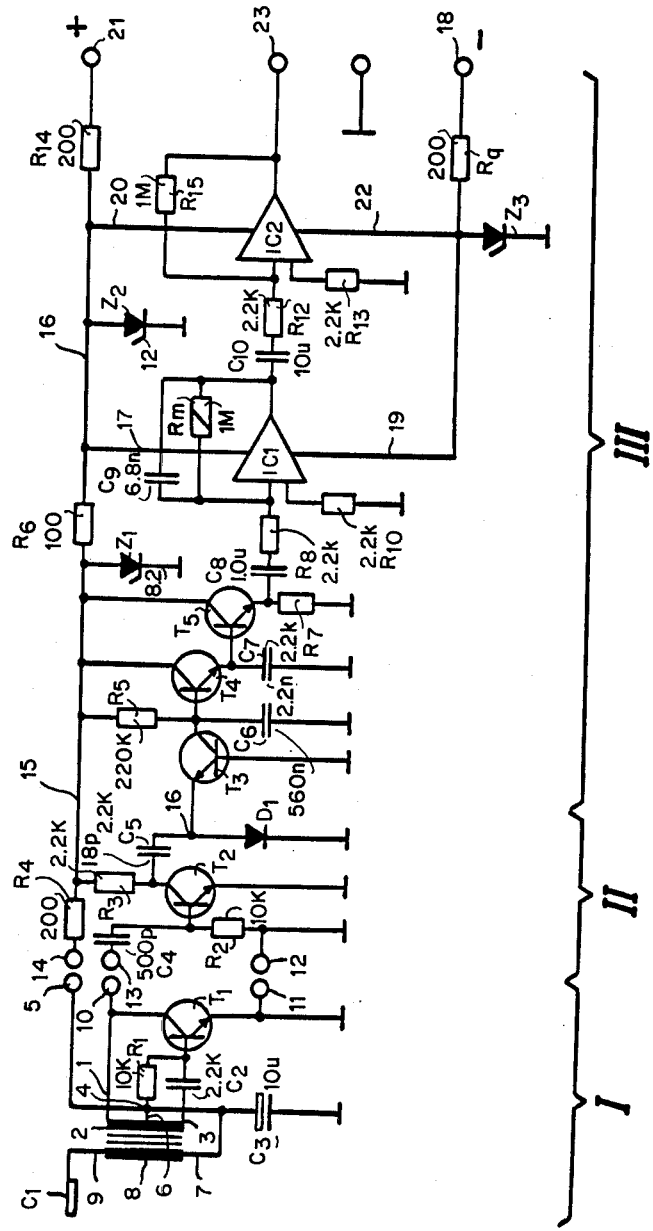

United States Patent [19]

Kessler et al.

[11] 4,035,696

[45] July 12, 1977

[54] APPARATUS FOR MONITORING MACHINE PARTS SUBJECT TO WEAR

[75] Inventors: Gerhard Kessler, Reudern; Peter Fuchs, Ebingen, both of Germany

[73] Assignee: Texmaco H.G. Kessler GmbH, Reudern, Germany

[21] Appl. No.: 575,980

[22] Filed: May 8, 1975

[30] Foreign Application Priority Data

May 14, 1974 Germany .......................... 2423330
Feb. 27, 1975 Germany .......................... 2508477

[51] Int. Cl.² ....................................... H01H 47/12
[52] U.S. Cl. ................................. 361/203; 331/65; 340/267 R
[58] Field of Search ........................ 66/157, 165; 317/DIG. 2, 146, 53, 246; 340/267 R; 331/65; 324/61 R, 61 P, 61 QS

[56] References Cited

U.S. PATENT DOCUMENTS

| | | | |
|---|---|---|---|
| 3,201,775 | 8/1965 | Pedersen | 317/DIG. 2 |
| 3,422,415 | 1/1969 | Ichimori | 331/65 X |
| 3,529,445 | 9/1970 | Brose | 66/165 X |

Primary Examiner—Harry E. Moose, Jr.
Attorney, Agent, or Firm—Martin A. Farber

[57] ABSTRACT

An apparatus for monitoring moving machine components, comprising a high-frequency oscillator circuit including a frequency determining element, the latter constituting an open capacitor connected in the oscillator circuit and having a capacitor face. The moving machine components to be monitored interact capacitively at least intermittently with the capacitor face of the open capacitor, and a high-frequency amplifier and signal limiter circuit is operatively connected to an output of the oscillator circuit, with a signal evaluating circuit operatively connected therewith.

11 Claims, 9 Drawing Figures

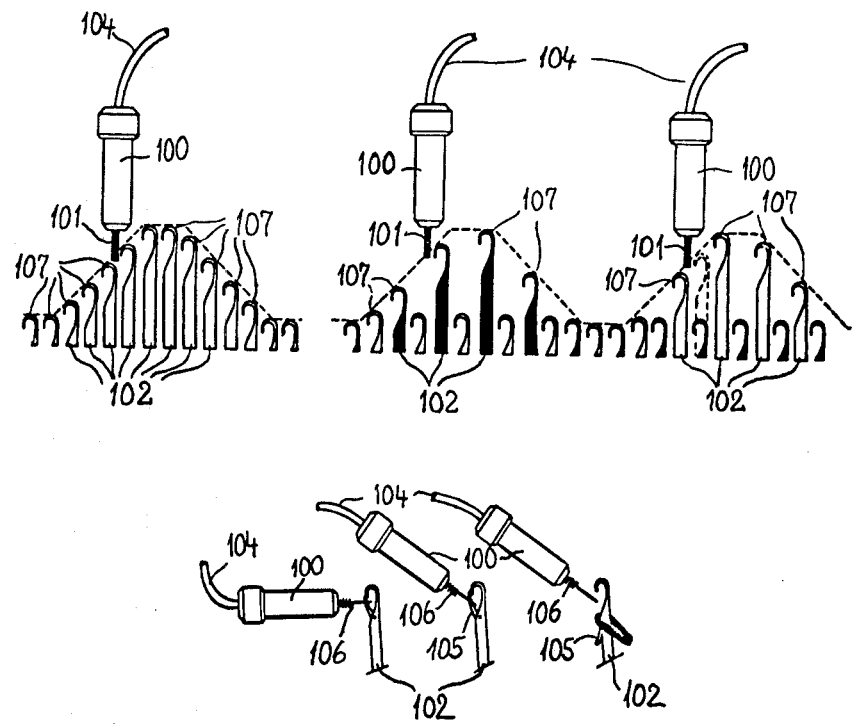
Fig.6
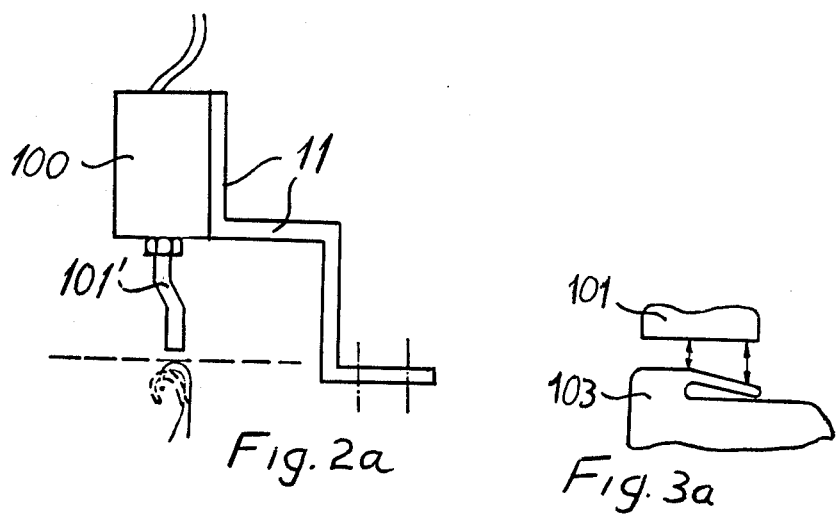
Fig.7
Fig.2a
Fig.3a

APPARATUS FOR MONITORING MACHINE PARTS SUBJECT TO WEAR

The present invention relates generally to an apparatus for monitoring and possibly controlling machines comprising parts and tools which are subject to wear and in particular to a stop motion device for textile machines in cases of damaged needles, sinkers or the like.

In the textile art a great variety of attempts have already been made to reduce costs by monitoring the machines used for working and processing textiles for proper operation in order to stop the system as soon as possible when faults occur.

In the monitoring of hoisery, knitting and netting machines for proper operation two fundamentally different techniques are employed.

The one technique is based on indirect monitoring by checking the material produced, any faults detected in the material leading to stopping the machine. This method has however the disadvantage that a relatively long length of fabric is made before a fault or flaw leads to stopping of the machine. The faulty material is usually waste which can increase costs considerably.

For this purpose, the increasing tendency today is to employ direct monitoring of the moving machine parts which participate in the looping operation by intermittently checking the state and function for example of the needles, sinkers, latches, or the like, by means of suitable scanning devices. This technique has the advantage that machine and tool faults can be detected very quickly so that the machine is stopped before any appreciable quantity of faulty material has been produced.

For direct monitoring, firstly optical means have been developed which however always fail when thread ends or fluff due to wear of the yarn worked obstruct the ray path, which is frequently the case and gives rise to an erroneous switching. The stoppage times of the machines monitored in this manner due to erroneous switchings however also increase costs considerably, making the product more expensive or reducing the profit margin.

Moreover, optical monitoring means are very complicated in construction and consequently expensive. Furthermore, because of their space requirement they cannot be used to monitor all the machine components.

To obviate the disadvantage of optical flaw and fault monitoring in knitting machines an inductively operating stop motion device has recently been developed which is not detrimentally effected by contaminations and comprises a test coil in the form of an elongated loop having a narrow slit-like opening through which the needles are passed. This changes the inductance of the coil by a predetermined amount whose magnitude depends on the magnetic mass of the needle. When the needle breaks or is damaged the mass thereof changes and this leads to a deviation of the inductance change in the test coil; the deviation of the inductance change is evaluated as control pulse for stopping the machine.

It has been found that a disadvantage of this latter known automatic stop motion means in textile machines is the fact that the dimensions of the test coil require a considerable amount of space and consequently because of this space requirement and the usually restricted space conditions in textile machines it is frequently not possible to arrange such coils in the region of the needles to be monitored and consequently only exposed machine components can be monitored.

Moreover, it is not possible in this manner to detect bent needles because the bending does not usually change the needle mass and consequently there is no inductance change in the test coil able to produce a stop signal.

It is therefore the problem underlying the present invention to provide a monitoring and stop motion apparatus in textile machines which operates with absolute reliability and which avoids both the contamination susceptibility of optical monitoring means and the restricted employability of inductive monitoring means so that the latter can be used in machines and machine components under confined space conditions.

According to the invention this problem is solved by a capacitively operating sensing means whose capacitance change in the case of a defective needle, sinker, latch or the like is used to monitor, control and possibly stop the machine.

According to a specific feature of the present invention the capacitance of the sensing means is connected as frequency-determining element into a high-frequency oscillator. Said high-frequency oscillator is integrated in the sensing head of the sensing means and produces the necessary control pulses.

In this manner, it is possible for the first time to directly monitor even difficultly accessible parts, such as sinkers in knitting machines.

Further details of the invention will be described in detail with the aid of an example of embodiment in conjunction with the associated drawings.

Figure 2:
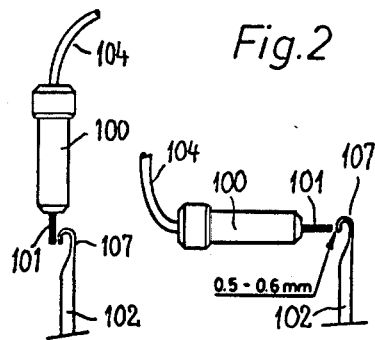
Figure 5:
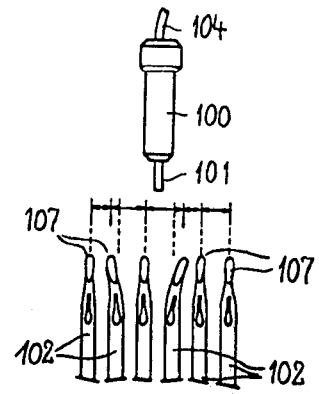
Figure 4:
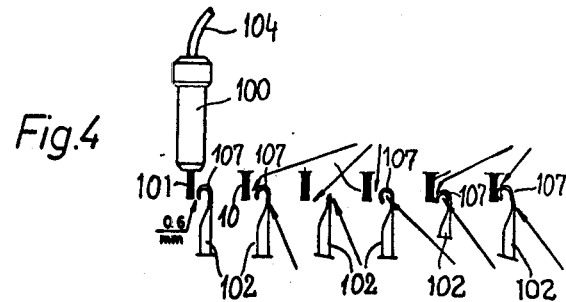
Figure 3:
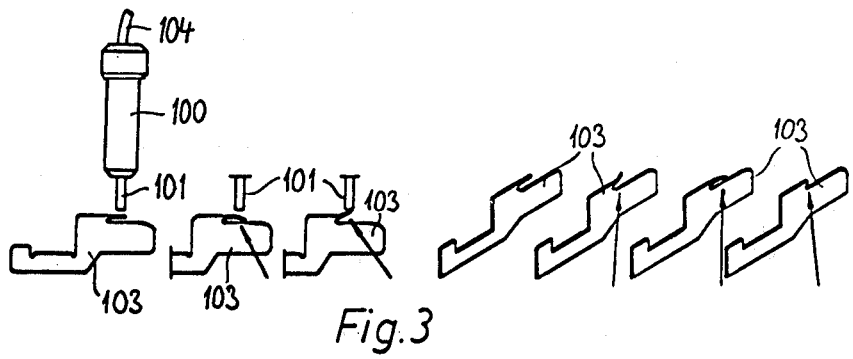

In the drawings:

FIG. 1 shows the circuit construction of a stop motion apparatus according to the invention FIG. 2 shows an example of embodiment of a sensing head in different sensing positions for monitoring a needle FIG. 2a shows a mounted, angled capacitor sensor FIGS. 3, 3a show arrangements of sensing heads according to the invention for monitoring sinkers FIGS. 4 and 5 show the detection of possible needle faults FIG. 6 shows basic arrangements of the sensing head with varied needle extension, and FIG. 7 shows the use of the sensing head according to the invention as needle latch monitor.

The example of embodiment described below of a capacitively operating monitoring apparatus is designed as stop motion device for use in hosiery, knitting or netting machines which responds to defective needles, sinkers, latches, and other movable machine components.

A corresponding circuit construction is illustrated in FIG. 1 and is accommodated in two separate constructional units which are connected together via electrical leads.

The embodiment as separate constructional units in the form of a sensing head I on the one side, and a pulse amplifier and limiter II as well as a signal evaluating circuit III on the other side, has the advantage that the sensing head 100 (cf. FIG. 2) can be made with very small dimensions so that concealed or difficultly accessible machine components can be more easily reached for monitoring.

Accommodated in the sensing head 100 is an HF oscillator I which is constructed as capacitively tunable oscillating circuit comprising an open capacitor C1.

The effective capacitor area C1 determining the frequency of the oscillator is lead as a pin 101 out of the sensing head 100. In the operating position the machine components to be monitored are disposed opposite said pin 101 as mutual capacitance.

The circuit illustrated in FIG. 1 of a capacitively tunable HF oscillator I consists of an HF transistor T1, for example of type BC 237 B of the Siemens AG, which is connected with its collector to the one end 1 of a primary coil 2 of a transformer comprising nine and a half turns of 0.15 mm thick Cu varnished wire whereas the other end 3 of said coil 2 is applied via a capacitor C2 of 2.2 nF to the base of the transistor T1. In addition, the base of the transistor T1 is connected via a resistor R1 of 10 Kohms to a junction 4 which in turn is connected to a terminal 5, a tap 6 of the coil 2 which branches 6 turns-from the end 1 thereof and to an end 7 of a secondary coil 8 of the transformer, said connection being applied to ground via an electrolytic capacitor C3 of 10 $\mu$F. The secondary coil 8 of the transformer is connected with its other end 9 to the frequency-determining open capacitor C1 of about 15 pF. The secondary coil 8 comprises 285 turns of enamelled copper wire having a thickness of 0.07 mm which are wound together with the turns of the primary coil 2 onto a bobbin of the type PL-7 of the material FXC3H1 of the Valvo company. The inductance of this transformer is 130 mH (milli henry). The collector of the transistor T1 is also connected to a socket 10; the emitter output of the transistor is connected to a socket 11 and also applied to ground.

The HF oscillator described above oscillates with a frequency of about 200 kHz and is accommodated in a cylindrical body having a diameter of about 12 mm and a length of about 52 mm, the frequency-determining capacitor C1 being led out as pin 101 at the lower portion of the housing. The operating frequency of 200 kHz can however be varied in wide limits without the functionability of the stop motion device being impaired, e.g., 40 to 800 kHz.

The HF oscillator forms the sensing head designated by 100 in FIGS. 2 to 7 which is electrically connected via a flexible 3-conductor electrical lead 104 to a second constructional unit which will be described in detail below.

The electrical conductor of the lead 104 connecting the sockets 11 and 12 which is connected to the socket 11 is constructed as hose-like shield which surrounds the two other electrical conductors connecting the sockets 10, 13 and 5, 14 together respectively. In this manner interference quantities are prevented from passing through the connecting lead 104 into the circuit and influencing the stop motion device.

The sensing head 100 need not necessarily be constructed as a cylinder but can assume any suitable three-dimensional form for the particular purpose. The individual circuit elements may take many different forms in this respect as regards their geometrical arrangement. Thus, the housing of the sensing head 100 may readily be given the form of a cube, a right parallelepiped, a sphere, or another suitable geometrical body. The pin 101 forming the open capacitor C1 may also have various forms, for example that shown in FIG. 7 at 106, or FIG. 3a. The pin may also be extended and suitably bent to enable the components to be monitored to be more easily approached, e.g., pin 101' in FIG. 2a, and may be mounted by angle member 11. The HF oscillator I is followed by an amplifying and limiting stage II with which the sinusoidal signal of the HF oscillator is amplified and converted to a rectangular signal of constant amplitude.

The two circuit groups are connected together via the aforementioned flexible three-conductor electrical lead 104, and are separately housed.

The amplifying and limiting stage II comprises a transistor T2, also of Type BC 237 B, the base of which is connected via a coupling capacitor C4 of 500 pF to the collector of the transistor T1 and simultaneously via a resistor R2 of 10 Kohms to the emitter of the transistor T1 and ground. Whereas the emitter of the transistor T2 is applied directly to ground, the collector is connected via a resistor R3 of 2.2 Kohms to the positive lead 15 which is led via a further resistor R4 of 200 ohms to the HF oscillator. The collector of the transistor T2 is also applied to ground via a capacitor C5 of 15 pF and a diode D1 of Type 1N4 148 of the Siemens AG. The useful signal is taken from the point 16 between the capacitor C5 and the diode D1 and converted to control pulses by the following evaluation circuit III.

The current change arising at the point 16 due to a frequency change of the HF oscillator I produced by a capacity change of the capacitor C1 is amplified by the transistor T3. For this purpose, the emitter output of the latter is connected to the point 16 and the collector thereof firstly via a resistor R5 of 220 Kohms to the positive lead 15 and secondly via a capacitor C6 of 560 nF to ground. The base of the transistor T3 is connected directly to ground. Like the transistors T4 and T5, which are connected as emitter follower, the transistor T3 is of Type BC 237 B. The transistor T4 is connected with its base directly to the collector output of the transistor T3 and its collector is applied to the positive lead 15. The emitter output of the transistor T4 is connected to the base of the transistor T5 and simultaneously applied via a capacitor C7 of 2.2 nF to ground. The collector output of the transistor T5 is again directly connected to the positive lead 15 which by means of the zener diode Z1 of Type ZF 8.2 of the Siemens AG is regulated to a voltage of 8.2 volts. For this purpose, a resistor R6 of 100 ohms is connected in the positive lead 16 in front of the zener diode Z1 and the latter is placed between the positive lead 15 and ground. The emitter output of the transistor T5 is connected on the one hand via a resistor R7 of 2.2 Kohms to ground and on the other via a capacitor C8 of 10 $\mu$F and a resistor R8 of 2.2 Kohms connected in series therewith to the input of an IC 1 of the Type SN 741 of the Siemens or Valvo companies. The current supply of the IC 1 is via a branch line 17 which branches from the positive lead 16 regulated to 12 volts by the zener diode Z2 of Type ZF 12 of Siemens AG and a second branch line 19 from the negative terminal 18 of a stabilized voltage source with interposition of a series resistance R9 of 200 ohms said line 19 being also regulated to 12 volts with respect to ground by means of a third zener diode Z3 of the Type ZF 12. The IC 1 is additionally connected via a resistor R10 of 2.2 Kohms to ground. The input and the ouput of the IC 1 are connected together via a trimming potentiometer R11 of 1 Mohms and a capacitor C9 of 6.8 nF connected in parallel therewith. The output of the IC 1 leads via a further capacitor C10 of 10 $\mu$F and a following resistor R12 of 2.2 Kohms to the input of a second IC 2 which is connected via a resistor R13 of 2.2 Kohms to ground and via a branch line 20 and a preceding resistor R14 of 200 ohms to the positive terminal 21 of a regulated voltage source and via a second branch line 22 to the negative terminal 18 of said voltage source. The input and the output of the IC 2 are connected via a resistor of 1 Mohms. In addition, the output of the IC 2 is led to the terminal 23 at which the control pulse for stopping the machine when a fault occurs is applied.

As already mentioned above, the capacitively tunable oscillator circuit I is accommodated with its open capacitor C1 in the sensing head 100 (cf. FIGS. 2 to 7), the effective capacitor area C1 determining the frequency of the oscillator circuit being led as pin 101 or 106 out of the sensing head. To monitor machine components the sensing head 100 is arranged in such a manner that the pin 101 or 106 is opposite the machine components to be monitored in such a manner that it is in capacitive interaction therewith at least at times.

FIG. 2 illustrates two possibilities of arranging a sensing head 100 in which the pin 101 is brought into the immediate vicinity of the needle 102 to be monitored. In this case, the pin 101 forms the one face of the capacitor C1 whereas the needle 102 or the heads thereof form the other capacitor face.

When a needle 102 approaches the pin 101 of the sensing head 100 the capacitance of the capacitor C1 changes, producing a change in the oscillating frequency of the oscillator I.

The arrangement of the sensing head 100 and the form of the pin 101 is such that as shown in FIG. 6 the pin 101 forming the one capacitor half C1 interacts with a plurality, at least two, of the needle heads 107 which on extension pass the pin. In this manner the passing needle heads 107 form a second substantially constant capacitor area so that only an insignificant frequency change of the oscillator I takes place. An appreciable capacitance change of the capacitor C1 does not take place until a damaged needle 102 passes the pin 101 as shown for example in FIGS. 4 and 5, this then initiating a corresponding stopping pulse in the follower circuit. In this manner, apart from monitoring the proper condition of the needle the proper needle extension can be checked.

Similarly, it is possible for the first time, as illustrated in FIG. 3, to monitor sinkers 103 to ensure they are in satisfactory condition. In this case as well, sinkers which have been depressed or drawn up or otherwise bent produce a capacitance change which leads to stopping of the knitting machine.

A further possible use of capacitive monitoring is shown in FIG. 7 in which the position of the latches 105 of the needles 102 is checked by means of the pin 106 forming the one capacitor face C1. In this case as well, the checking of the latch position is carried out in the manner described above in conjunction with the monitoring of needles.

The great variety of possible uses in monitoring by means of the circuit arrangement according to the invention for detecting all kinds of machine faults is due to the fact that a capacitance change of the capacitor C1 is caused both in the case of a differing approximation of the components forming the mutual capacitance, i.e., the needle 102, 107, sinkers 103, needle latches 105 or other machine components, due to deformation, bending or incomplete extension thereof as well as to differing mass thereof due to broken off parts and the resulting changed counter face of the capacitor C1.

Particularly advantageous with the circuit arrangement is the fact that a plurality of sensing heads I may be combined and connected to the amplifying and evaluating circuit II and III. In addition, depending on the spatial conditions in any given case, the sensing head 100 may be disposed at a different location and position with respect to members to be monitored.

With the sensing head 100 of small construction, machine components can for example also be monitored at points where they do not reach their terminal position and are therefore difficultly accessible.

In the example of embodiment of the circuit illustrated in FIG. 1 for a stop motion according to the invention in knitting machines a counting circuit is provided in the evaluating stage III to obviate erroneous switchings due to so-called "spraying needles". The time-dependent counting stage operates so that the machine is stopped only after repeated presence of a periodic fault signal, whereas in the case of a single fault signal which does not recur and which could for example have been caused by a spraying needle no stopping signal is passed to the relay stage when no further periodic fault signal occurs. As a result of this step, the machine is stopped only when "genuine" machine faults are present and any unnecessary stoppages of the system eliminated.

The invention thus resides in a device using the characteristics of a capacitor on an alternating voltage, the device being mounted over the gliding positions of the sinkers or needle heads, for example, and is subject to an alternating sinusoidal voltage which may preferably be under 24 volts, although not limited thereto. The open capacitor face may be under voltage and the adjacent moving components of the machine to be monitored which constitute the other capacitor face may be grounded. When the needles or sinkers move in constant spacing relative to and past the device, this indicates that no damage is in the moving machine components. When the spacing varies, e.g., due to a damaged pressed-in, broken, or extended needle or sinker, the frequency of the oscillator changes, which is transformed into a switching or control pulse for stopping the machine.

While we have disclosed several embodiments of the invention it is to be understood that these embodiments are given by example only and not in a limiting sense.

We claim:

1. An apparatus for monitoring moving machine components, comprising
   a high-frequency oscillator circuit including a frequency determining element, the latter constituting an open capacitor connected in said oscillator circuit and having a capacitor face,
   said moving machine components to be monitored constituting means for interacting capacitively at least intermittently with said capacitor face of said open capacitor,
   said oscillator circuit including means for providing a considerable change in operating oscillating frequency thereof as a result of a very small capacitance change of said open capacitor interacting with the moving machine components to be monitored, the change in oscillating frequency constituting a control signal,
   a high-frequency amplifier and signal limiter circuit operatively connected to an output of said oscillator circuit operatively receiving said control signal, and a signal evaluating circuit operatively connected therewith.

2. The apparatus as in claim 1 further comprising
a sensing head contains said high-frequency oscillator circuit as a construction unit therein, said capacitor face constituting a pin projecting from said sensing head to adjacent said moving maching components,
a flexible three-conductor electrical lead connects said output of said oscillator circuit to an input of said high-frequency amplifier and signal limiter circuit.

3. The apparatus as in claim 1 wherein
said open capacitor is formed with area means disposed adjacent said moving machine components for interacting capacitively with simultaneously at least two of said moving machine components, whereby only a change in the condition of at least one of the latter causes a change in the operating oscillating frequency.

4. The apparatus as in claim 1 wherein
said high-frequency oscillator circuit on the one hand, and said high-frequency amplifier and signal limiter circuit and said signal evaluating circuit on the other hand are constructed as spatially separated circuit units,
a flexible electrical lead connects said circuit units.

5. The apparatus as in claim 1 wherein
said high-frequency oscillator circuit comprises an inductor and a transistor as well as said capacitor operatively connected together.

6. The apparatus as in claim 1 wherein
said high-frequency oscillator circuit has a fundamental frequency of substantially 200 kHz.

7. The apparatus as in claim 1 wherein
said high-frequency oscillator circuit has a fundamental frequency which is substantially within the limits of 40 kHz to 800 kHz.

8. The apparatus as in claim 1 wherein
said signal evaluating circuit constitutes a time-dependent counting circuit means for supplying a control pulse only when a periodic fault signal is present.

9. The apparatus as in claim 1 wherein
said moving machine components constitute needle heads, sinkers, needle latches and extensions thereof of hosiery, knitting and netting machines.

10. The apparatus as in claim 1 wherein
said high-frequency oscillator circuit is tuned in a normal condition thereof, and becomes detuned by a change in capacitance of said capacitor in a presence of a defective of said moving machine components, and a machine in which said moving machine components are operatively disposed is operatively connected to said oscillator circuit, the latter constituting operative means for stopping said machine when said oscillator circuit becomes detuned by said change in capacitance of said capacitor.

11. The apparatus as in claim 1, wherein
said high-frequency oscillator comprises,
a high frequency transistor having a base, a collector and an emitter, the latter being grounded,
a transformer having a primary coil, the latter having one end connected to said collector, and having a secondary coil,
a capacitor connected between said base of said transistor and the other end of said primary coil,
a junction connected to one end of said secondary coil and a tap of said primary coil,
a resistor connected between said base and said junction,
an electrolytic capacitor connecting said junction to ground,
the other end of said secondary coil is connected to said open capacitor.

* * * * *